United States Patent [19]

Cherukuri et al.

[11] Patent Number: 5,059,416

[45] Date of Patent: Oct. 22, 1991

[54] ZINC COMPOUND DELIVERY SYSTEM WITH IMPROVED TASTE AND TEXTURE

[75] Inventors: Subraman R. Cherukuri, Towaco; Tommy L. Chau, Bridgewater, both of N.J.

[73] Assignee: Warner-Lambert Company, Morris Plains, N.J.

[21] Appl. No.: 372,394

[22] Filed: Jun. 26, 1989

[51] Int. Cl.$^5$ .......................... A61K 9/68; A61K 7/16; A61K 33/30; A61K 9/14
[52] U.S. Cl. ........................................ 424/48; 424/439; 424/440; 424/49; 424/51; 424/52; 424/55; 424/57; 424/641; 424/643; 424/492; 424/493; 424/496; 424/497; 424/498; 424/54; 514/974
[58] Field of Search .......................... 424/48, 492–498, 424/642; 426/303; 514/974, 965

[56] References Cited

U.S. PATENT DOCUMENTS

| | | | |
|---|---|---|---|
| 2,828,206 | 3/1955 | Rosenberg | 424/498 |
| 3,080,294 | 3/1963 | Shepard | 424/498 |
| 3,879,511 | 4/1975 | Goodhart et al. | 424/498 |
| 4,469,674 | 9/1984 | Shah et al. | 424/643 |
| 4,582,709 | 4/1986 | Peters et al. | 424/643 |
| 4,867,989 | 9/1989 | Silva et al. | 424/48 |

OTHER PUBLICATIONS

Grant et al., ed., Grant & Hackh's Chemical Dictionary, 5th ed., McGraw-Hill, 1987, p. 379.
Budavari et al., ed., Merck Index, 11th ed., Merck, 1989, pp. 4484–4485.

*Primary Examiner*—Thurman K. Page
*Assistant Examiner*—Edward J. Webman
*Attorney, Agent, or Firm*—Daniel A. Scola, Jr.; Craig M. Bell

[57] ABSTRACT

A new delivery system for zinc compounds and the process for its preparation is disclosed, which has use in a variety of products including comestibles such as chewing gum compositions, confections, pharmaceuticals, food products such as vitamin preparations, dentifrice compositions and throat lozenges. More particularly, this invention relates to a process for preparing a zinc compound delivery system comprised of a zinc core material coated with a first hydrophilic coating comprising a hydrocolloid material and a second hydrophobic coating selected from the group consisting of fats, waxes and mixtures thereof. The delivery system provides enhanced masking of the bitter flavor characteristic of zinc compounds, as well as reduced grittiness with retained stability at the elevated temperatures of product formulation.

19 Claims, 3 Drawing Sheets

ZINC COMPOUND DELIVERY SYSTEM WITH IMPROVED TASTE AND TEXTURE

The present invention relates generally to zinc compounds that are useful for example, as deodorants, food additives and nutritional supplements, and particularly to the preparation of such zinc compounds in a form to reduce their inherent bitterness and grittiness.

The metal zinc is well-known for its use in a variety of orally accepted products ranging from mouthwashes and dentifrices to nutritional supplements. Zinc is prepared in a variety of compounds including inorganic salts such as the halides, nitrates and sulfates, and organic compounds including the acetates, citrates, gluconates, and compounds with various amino acids and vitamins. These compounds have been formulated into solid and liquid compositions for a variety of hygienic and nutritional purposes and presently enjoy particular popularity and value in such connection.

One of the major drawbacks of the incorporation of zinc compounds into various orally received products has been the characteristic metallic bitterness of zinc that is experienced as soon as the zinc compound is released and proceeds to break down in the mouth. A variety of formulations have been prepared and attempted for the purpose of lessening or masking entirely the bitter aftertaste of zinc compounds.

Thus, the zinc active has been disposed in a variety of media including combination with flavors and with other compounds in an attempt to achieve a neutralizing or masking effect on the bitter aftertaste of zinc. However, none of the presently known techniques and compositions appear to offer the desired abatement of zinc aftertaste.

Thus, U.S. Pat. Nos. 4,684,528 and 4,758,439, both to Godfrey, disclose the formulation of zinc compounds with particular amino acids which the patentee indicates serves to reduce the unpalatable and undesirable aftertaste of prior zinc formulations. Godfrey describes at great length the nutritional and therapeutic potential of zinc and likewise identifies the objections raised by recipients of zinc containing products, among them "distortion of taste" and "mouth irritation". Godfrey proposes the preparation of zinc compounds with the amino acids glycine, alanine, aminobutyric acid, valine, isovaline, leucine, isoleucine and lysine.

The value of zinc as an astringent and as a dentifrice is identified in U.S. Pat. No. 4,689,214 to Niles et al. and in corresponding United Kingdom Patent Application 2,187,642A to Barth et al. In both disclosures, the inventors suggest the preparation of a zinc compound in combination with an ionone ketone terpene compound on the basis that the latter serves to mask or otherwise neutralize the undesirable flavors and aftertaste of the zinc compound. In Niles et al., the combination of the ionone terpene derivative and zinc is suggested to offer an improvement over the undesirable taste imparted by the zinc alone, and to extend the activity of zinc in combatting mouth odor. Both Niles et al. and Barth et al. discuss the numerous applications of zinc compounds in the area of oral hygiene, including its capabilities in fighting plaque, calculus, mouth malodor and as an antiseptic and corrective of oral conditions such as pyorrhea.

The encapsulation of actives is well-known for a variety of purposes, among them to protect the active from degradation in contact with other agents in a given product or composition; to modulate the release of the active, as in the instance of flavor and sweeteners, and to render the active capable of withstanding rigorous processing conditions during formulation into products. Efforts have also been made in various instances to render actives more palatable likewise by enrobing or encapsulating the active in one fashion or another. The following representative techniques are noted in the art with respect to differing actives.

U.S. Pat. No. 4,384,004 to Cea et al. discloses solid particles of aspartame encapsulated by a coating material selected from the group consisting of cellulose, cellulose derivatives, arabinogalactin, gum arabic, polyolefins, waxes, vinyl polymers, gelatin, zein and mixtures thereof, wherein the amount of said coating material to said methyl ester is from 1:1 to 1:10. The objective of this invention is to provide protection to the active and to delay its release.

U.S. Pat. No. 3,867,556 to Darragh et al. also encapsulates volatile flavors in a fat or wax material. The patentees had found that the fat/wax encapsulation displayed excessive instability to heat, and as their product was intended primarily for incorporation into baked goods, they applied a second coat of a water-soluble material such as gum arabic, which would provide high temperature stability while conferring rapid disintegration on contact with moisture.

The above noted and other known techniques have heretofore provided no insight into the problem of concealing the bitter aftertaste of the zinc active, while at the same time permitting the active to function in a timely manner and with improved mouthfeel in the products to which it is desirably added. A need therefore exists for the development of a zinc compound delivery system which remedies the aforenoted problems by preventing or at least minimizing the bitterness of the compound while at the same time permitting timely release of the active and promoting improved textural properties and favorable high temperature stability.

SUMMARY OF THE INVENTION

In accordance with the present invention, a zinc compound delivery system is disclosed which comprises a composite having improved flavor masking and temperature stability characteristics, and smoother texture and mouthfeel when incorporated into lozenges, chewing gums and other products. The zinc compound delivery system is prepared with a core material comprising a zinc compound selected from inorganic and organic compounds of zinc; a first hydrophilic coating comprising a film forming hydrocolloid material in an amount of from about 10% to about 50% by weight, and preferably from about 10% to about 25% by weight of the core material; and a second hydrophobic coating comprising a fat and/or wax component in an amount of from about 20% to about 100% by weight, and preferably from about 20% to about 50% by weight of the combined core material and first coating. In effect, the present invention is a dual encapsulation system for delivering zinc compounds while masking the unpleasant taste of such compounds. In a particularly preferred embodiment, the first coating is present in an amount of 25% by weight of the core material, and the second coating is present in an amount of 50% by weight of the combined core material and first coating.

Suitable zinc compounds include inorganic salts such as the halides, nitrates, sulfates and chromates; and organic compounds such as the gluconates, acetates, tartrates and salicylates. Hydrocolloid materials include pectins, alginates, cellulose and its derivatives, gelatin, gums, mucilages, and mixtures. The gelatin used herein possesses a bloom strength on the order of 250 or higher, which is desirable to form a strong and resilient coating on the zinc active.

The fat or wax component comprises fats, including fatty acids such as hydrogenated and partially hydrogenated oils; mono-, di-and triglycerides, polyglycerol esters and sorbitol esters. Waxes include natural and synthetic waxes, with representative waxes comprising polyolefin waxes, paraffin wax, beeswax, microcrystalline wax, and mixtures.

The zinc compounds are prepared into the core material by standard processes such as spray drying and fluidized bed coating, and may optionally be prepared with additives such as excipients, including bulking agents, fillers, and the like. Suitable excipients include sugar, mannitol, sorbitol and maltodextrin.

The zinc compound delivery system is produced by a process which comprises forming the zinc compound and optionally one or more excipients into a first core material, applying the first coating to this core material preferably by fluidized bed coating, and then spray congealing the second fat and/or wax coating over the particles thus formed. In the instance where the core material comprises zinc sulfate or zinc gluconate, it is preferable to mill the particles initially formed to a size ranging to at least 30 mesh (590 microns) and to screen the formed particles before coating to enhance uniformity in the final product.

The zinc delivery system may be incorporated into a variety of foods and confections, including chewing gums and hard candies, as well as pharmaceutical and nutritional preparations, as a deodorant in oral rinses, in tooth pastes and in throat lozenges. The present invention therefore includes chewing gums and hard candies, pharmaceutical and personal hygiene products such as dentifrices and mouthwashes, and nutritional supplements, all incorporating the present zinc compound delivery system.

Accordingly, it is a principal object of the present invention to provide a zinc compound delivery system that offers improved aftertaste masking characteristics.

It is a further object of the present invention to provide a zinc compound delivery system as aforesaid which provides improved taste masking and mouthfeel in combination with temperature stability and high processing temperature capability.

It is a still further object of the present invention to provide pharmaceutical products, nutritional supplements, personal hygiene, confectionery and comestible products, all having contained therein the zinc compound delivery system of the present invention.

Other objects and advantages will become apparent to those skilled in the art from a consideration of the ensuing description which proceeds with reference to the following illustrative drawings.

DETAILED DESCRIPTION

In accordance with the present invention, a delivery system for a zinc compound is disclosed which offers reduced bitterness and improved mouthfeel with desirable high temperature stability. The present delivery system accordingly comprises:

(a) a core material comprising a zinc compound selected from the group consisting of inorganic salts of zinc, organic salts of zinc, and mixtures;

(b) a first hydrophilic coating comprising a hydrocolloid material in an amount of from about 10% to about 50% by weight of the core material; and (c) a second hydrophobic coating selected from the group consisting of fats, waxes, and mixtures thereof, present in an amount of from about 20% to about 100% by weight of the combination of the core material and the first hydrophilic coating.

More particularly, the delivery system of the present invention comprises the core material with the first coating present in an amount of from about 10% to about 25% by weight of the core material, and the second coating present in an amount of from about 20% to about 50% by weight of the combination of the core material and the first coating. As indicated earlier herein, the preferred embodiment contemplates the presence of the first coating in an amount of 25% by weight of the core material, and the second coating in an amount of 50% by weight of the combination of the core material and the first coating.

The zinc compounds in accordance with the present invention include both inorganic and organic zinc salts and, in particular, salts such as the halides, nitrates, sulfates, chromates, silicates, and compounds comprising complexes of these materials constitute the inorganic salts contemplated herein. Organic salts of zinc include zinc gluconate, zinc tartrate, zinc formate, zinc phenolsulfonate, zinc salicylate, zinc succinate, zinc glycerophosphate, zinc orotate, zinc aspartate, zinc picolinate, and other zinc salts formed with amino acids as per U.S. Pat. No. 4,758,439 to Godfrey.

Particular zinc halides include zinc chloride, zinc bromide, zinc iodide, zinc fluoride, and mixtures. Likewise, complexes of zinc compounds useful in a variety of astringent and deodorant capacities include such compounds as zinc glycerophosphate, zinc phenolsulfonate, zinc fluorosilicate, zinc fluorozirconate, and the like. The foregoing list is not intended to be inclusive but is merely representative of various zinc compounds both simple and complex that are contemplated in accordance with the present invention.

The zinc compounds may optionally be formulated with one or more excipients. Such excipients may be selected from the group consisting of carbohydrate materials, polyhydric alcohols and mixtures thereof. Carbohydrates useful as excipients include traditional water-soluble sweetening agents such as monosaccharides, disaccharides and polysaccharides such as xylose, ribose, glucose, lactose, mannose, galactose, fructose, dextrose, sucrose, sugar, maltose, partially hydrolyzed starch, or corn syrup solids and sugar alcohols such as sorbitol, xylitol, mannitol and the like, and mixtures thereof. The excipients are generally present in amounts of up to about 80% by weight of the core material and can be mixed in combination with each other or used individually.

The first coating of the present invention comprises a hydrophilic material and particularly a film forming hydrocolloid. The hydrocolloid may be generally selected from the group consisting of gums, pectins, alginates, mucilages, and mixtures thereof. Specifically, the hydrocolloid may a material selected from the group consisting of gum arabig, tragacanth, karaya, ghatti, agar, alginates, carrageenans, fuercellaran, psyllium, and mixtures thereof. The hydrocolloid may also be selected from polyvinyl pyrrolidone, gelatin, dextran, xanthan, cellulose, methylcellulose, ethylcellulose, hydroxyethyl cellulose, hydroxypropyl cellulose, hydroxypropyl methylcellulose, carboxymethyl cellulose, low methoxy pectin, propylene glycol alginate, and mixtures thereof.

Materials suitable for the preparation of the second coating include the fats and/or waxes. Suitable fats include fatty acids such as hydrogenated or partially hydrogenated oils, with representative materials comprising palm oil, palm kernel oil, soybean oil, cottonseed oil, peanut oil, rapeseed oil, rice bran oil, sunflower oil, safflower oil, and mixtures thereof. Other materials also useful as fats herein may be selected from monoglycerides, diglycerides, triglycerides, polyglycerol esters, sorbitol esters, and mixtures thereof.

Suitable waxes include natural waxes, synthetic waxes, and mixtures thereof, and in particular, comprise materials selected from the group consisting of paraffin wax, beeswax, carnauba wax, candelilla wax, lanolin wax, bayberry wax, sugar cane wax, petrolatum, CARBOWAX (Polyethylene glycol) spermaceti wax, rice bran wax, microcrystalline wax, and mixtures thereof. Naturally the foregoing is illustrative and not restrictive of suitable materials for inclusion in the delivery system of the invention, and the invention is considered to extend to unnamed equivalent materials within its scope.

The preparation of the coated zinc compound delivery system may be accomplished by a variety of agglomerative and/or coating techniques known in the art including, spray drying, fluidized bed coating techniques and the like, as disclosed in U.S. Pat. No. 4,384,004 to Cea et al. Preferably, fluidized bed coating may be employed to form the initial core as well as to apply the first and second coatings. In the fluidized bed procedure as applied herein, initially liquid droplets and subsequently, particles of the core material are suspended in an apparatus that creates a strong upward air current or stream in which the particles move. The stream passes through a zone of finely atomized coating material which causes the passing particles to be coated, after which the coated particles move from the upward stream and travel downward in a fluidized condition countercurrent to a flow of heated fluidized gas whereupon they are dried. The particles may reenter the upward stream for a further coating or may be withdrawn from the coating apparatus. The foregoing method and apparatus are known as the Wurster Process and are set forth in detail in the following U.S. Patents, the disclosures of which are incorporated herein by reference: U.S. Pat. Nos. 3,089,824; 3,117,027; 3,196,827; 3,241,520; and 3,253,944.

The first coating material is prepared for use by the formation of a liquid capable of being uniformly atomized. Thus, the water soluble hydrocolloid materials may be prepared as aqueous solutions. If desired, other ingredients such as plasticizers may be added to improve the properties of the final coating. Suitable plasticizers include the glyceryl ester of sebacic acid, diethyl phthalate, glyceryl triacetate, tributyl citrate, acetylated monoglyceride, citric acid ester of monodiglyceride, adipate ester, and others. The plasticizers may be added in known effective amounts within the scope of the invention.

While the second hydrophobic coating is preferably applied to the core material coated with the first coating by a fluidized bed coating technique as described above, the technique known as spray congealing may also be used. In this technique, the fat or wax material is heated to a temperature of about 75° to about 95° C. and placed under low shear mixing, after which the core material coated with the hydrophilic coating is added and mixed at high shear to achieve a uniform dispersion of the core materials therein. The dispersion is then fed into a heat controlled spray nozzle and is spray congealed. The term "spray congealing" as used herein refers to the solidification of the atomized liquid droplets which cool and solidify upon hitting the cooler temperature of the surrounding atmosphere, which may, for example, be on the order of 25° C. The nozzle pressure is regulated to control particle droplet size, and droplets cool and congeal once they are emitted from the nozzle and contact the cooler environment. The result of this process is a dry particle or agglomerate which may have an approximate elliptical or spherical shape.

The resultant product of this invention is in powder or granulated form. The particle size is not critical to the delivery system and can be adjusted to accommodate a particular desired release rate and mouthfeel, depending on the vehicle, e.g., chewing gum, confection, pharmaceutical, oral preparation or dentifrice, in which it is incorporated. The core material can include a wide variety of materials such as sweeteners, medicaments, drugs, flavoring agents, and the like in addition to the desired zinc compounds. These materials can be used either singly or in combination in either a single or multiple delivery system. That is, one or more of these materials may be present within one coating matrix or separately coated by the matrix and employed alone or in combination in a final product.

The instant delivery system can be incorporated in a number of ingestible products such as confections and the like, as well as chewing gum compositions, pharmaceutical preparations and denture products.

In accordance with a further embodiment, the present invention includes a chewing gum composition offering improved flavor intensity and longevity, comprising a gum base, a flavorant, a sweetener and a zinc compound delivery system comprising:

(a) a core material comprising a zinc compound selected from the group consisting of inorganic salts of zinc, organic salts of zinc, and mixtures;

(b) a first hydrophilic coating comprising a hydrocolloid material in an amount of from about 10% to about 50% by weight of the core material; and (c) a second hydrophobic coating selected from the group consisting of fats, waxes, and mixtures thereof, present in an amount of from about 20% to about 100% by weight of the combination of the core material and the first hydrophilic coating.

With regard to chewing gum formulations in which the novel delivery system is employed, the amount of gum base employed will vary greatly depending on various factors such as the type of base used, consistency desired and other components used to make the final product. In general, amounts of about 5% to about 85% by weight of the final chewing gum composition are acceptable for use in chewing gum composition with preferred amounts of about 15% to about 70% by weight. The gum base may be any water-insoluble gum base well known in the art. Illustrative examples of suitable polymers in gum bases include both natural and synthetic elastomers and rubbers. For example, those polymers which are suitable in gum bases include, without limitation, substances of vegetable origin such as chicle, jelutong, gutta percha and crown gum. Synthetic elastomers such as butadiene-styrene copolymers, isobutylene-isoprene copolymers, polyethylene, polyisobutylene and polyvinylacetate and mixtures thereof are particularly useful.

The gum base composition may contain elastomer solvents to aid in softening the rubber component. Such elastomer solvents may comprise methyl, glycerol or pentaerythritol esters of rosins or modified rosins, such as hydrogenated, dimerized or polymerized rosins or mixtures thereof. Examples of elastomer solvents suitable for use herein include the pentaerythritol ester of partially hydrogenated wood rosin, pentaerythritol ester of wood rosin, glycerol ester of wood rosin, glycerol ester of partial dimerized rosin, glycerol ester of polymerized rosin, glycerol ester of tall oil rosin, glycerol ester of wood rosin and partially hydrogenated wood rosin and partially hydrogenated methyl ester of rosin, such as polymers of alpha-pinene or beta-pinene; terpene resins including polyterpene and mixtures thereof. The solvent may be employed in an amount ranging from about 10% to about 75% and preferably about 45% to about 70% by weight to the gum base.

A variety of traditional ingredients such as plasticizers or softeners such as lanolin, stearic acid, sodium stearate, potassium stearate, glyceryl triacetate, glycerin and the like, for example, natural waxes, petroleum waxes, such as polyurethane waxes, paraffin waxes and microcrystalline waxes may also be incorporated into the gum base to obtain a variety of desirable textures and consistency properties. In accordance with the invention, however, these ingredients may be reduced in amount or in some cases, may be eliminated entirely. When present, these individual additional materials are generally employed in amounts of up to about 15% by weight and preferably in amounts of from about 3% to about 10% by weight of the final gum base composition.

Useful flavoring agents may be chosen from synthetic flavoring liquids and/or liquids derived from plants, leaves, flowers, fruits, etc., and combinations thereof. Preferably, the flavor component is selected from spearmint oil, cinnamon oil, oil of wintergreen (methylsalicylate) and peppermint oils. Also useful are artificial, natural or synthetic fruit flavors such as citrus oil including lemon, orange, grape, lime and grapefruit and fruit essences including apple, strawberry, cherry, pineapple and so forth.

The amount of flavoring agent employed is normally a matter of preference subject to such factors as flavor type, base type and strength desired. In general, amounts of about 0.05% to about 3.0% by weight of the final chewing gum composition are usable with amounts of about 0.3% to about 2.5% being preferred and about 0.7% to about 2.0% being most preferred.

In the instance where sweeteners are utilized in addition to those that may be included in the delivery system, the present invention contemplates the inclusion of those sweeteners well known in the art, including both natural and artificial sweeteners. Thus, additional sweeteners may be chosen from the following non-limiting list: sugars such as sucrose, glucose (corn syrup), dextrose, invert sugar, fructose, and mixtures thereof, saccharine and its various compounds such as the sodium or calcium compound; cyclamic acid and its various compounds such as the sodium compound; the dipeptide sweeteners such as aspartame; dihydrochalcone compounds, glycyrrhizin; *Stevia Rebaudiana* (Stevioside); chloro derivatives of sucrose; dihydroflavinol; hydroxyguaiacol esters; L-amino dicarboxylic acid gem-diamines; L-aminodicarboxylic acid aminoalkenoic acid ester amides; and sugar alcohols such as sorbitol, sorbitol syrup, mannitol, xylitol, and the like. Also contemplated as an additional sweetener is the nonfermentable sugar substitute (hydrogenated starch hydrolysate) which is described in U.S. Pat. No. Re. 26,959. Also contemplated is the synthetic sweetener 3,6-dihydro-6-methyl-1-1,2,3-oxathiazin-4-one-2,2-dioxide, particularly the potassium (acesulfame-K), sodium and calcium compounds thereof as described in German Patent No. 2,001,017.7.

Suitable auxiliary flavorings including both natural and artificial flavors, and mints such as peppermint, menthol, artificial vanilla, cinnamon, various fruit flavors, both individual and mixed, and the like are contemplated. The flavorings are generally utilized in amounts that will vary depending upon the amount of the flavor delivery system employed and may, for example, range in amounts of up to about 2% by weight of the final chewing gum composition weight. Thus, flavorings may be presented in the delivery system, in the chewing gum composition itself, or both.

The colorants useful in the present invention include the pigments such as titanium dioxide, that may be incorporated in amounts of up to about 1% by weight, and preferably up to about 0.06% by weight. Also, the colorants may include other dyes suitable for food, drug and cosmetic applications, and known as FD&C dyes and the like. The materials acceptable for the foregoing spectrum of use are preferably water-soluble. Illustrative examples include indigoid dye, known as FD&C Blue No. 2, which is the disodium compound of 5,5'-indigotindisulfonic acid. Similarly, the dye known as FD&C Green No. 1 comprises a triphenylmethane dye and is the monosodium compounds of 4-[4-N-ethyl-p-sulfobenzylamino)diphenylmethylene]-[1-(N-ethyl-N-p-sulfoniumbenzyl)-2-5-cyclohexadieneimine]. A full recitation of all FD&C and D&C and their corresponding chemical structures may be found in the *Kirk-Othmer Encyclopedia of Chemical Technology*, in Volume 5, pages 857–884, which text is accordingly incorporated herein by reference.

The chewing gum composition may additionally include fillers such as aluminum hydroxide, alumina, aluminum silicates, calcium carbonate, and talc and combinations thereof. These fillers may also be used in the gum base in various amounts. Preferably, the amount of fillers when used will vary from about 4% to about 30% by eight of the final chewing gum.

The chewing gums of the invention may be in any form known in the art, such as stick gum, slab gum, chunk gum, shredded gum, hard-coated gum, tableted gum, as well as center-filled gum.

A representative process for preparing a chewing gum composition including the inventive zinc compound delivery system is as follows. The gum base is melted (about 85° to about 90° C.), cooled to 78° C. and placed in a pre-warmed (60° C.) standard mixing kettle equipped with sigma blades. Any emulsifier for the gum base is then added and mixed in. Next, a portion of sorbitol and any glycerin is added and mixed in for an additional 3 to 6 minutes. The mixing kettle is cooled and mannitol, and the remainder of the sorbitol and glycerin are then added and mixing is continued. At the time, the unflavored chewing gum temperature is about 39°-50° C. The flavor is added and the present delivery system may then be added and incorporated into the base, and mixing is thereafter continued. Finally, the sweetener material is added and mixed for an additional 1 to 10 minutes. The final gum temperature is about 39° C.-50° C. The chewing gum composition is then discharged from the kettle, rolled, scored and formed into chewing gum pieces.

As indicated herein, the delivery system of the present invention may be incorporated into a variety of hard candies such as lozenges and the like. Such candies may be prepared by procedures as well-known in the art. Thus, a candy base which may comprise a sugar or sugar alcohol such as sucrose, fructose, glucose, lactose, polydextrose, mannitol, sorbitol, maltitol, corn syrup, hydrolyzed starch and the like, is subjected to heating at temperatures ranging up to around 250° F. to 300° F. in an open kettle, during which time additives such as flavor and colorants are included. Likewise, the zinc compound delivery system of the present invention may then be incorporated therein. After all ingredients are included, the resulting candy base is processed by a technique known as "pulling" which constitutes the literal hand stretching of the candy base mass to uniformly blend all of the ingredients therein. After "pulling" is complete, the resulting mass may be laid flat or otherwise disposed on a flat sheet and allowed to cool, during which time individual portions may be prepared. Naturally, the foregoing general description of hard candy manufacture is merely exemplary and presented herein for purposes of describing a best mode for carrying out one embodiment of the invention.

The present zinc compound delivery system may also be incorporated into a variety of dental preparations including toothpastes, mouthwashes, tooth polishes and the like, and the following exemplary description relates to the formulation of such products.

The vehicle in a toothpaste, often referred to as a dental vehicle, contains liquids and solids. In general, the liquid comprises water and often a humectant such as glycerine, sorbitol, propylene glycol or polyethylene glycol 400 including suitable mixtures thereof. It is usually advantageous to use a mixture of both water and one or two humectants. The total liquid content is generally about 20-90% by weight of the vehicle. The liquid content of the toothpaste generally includes about 5-40% of water. The preferred humectants are glycerine and sorbitol, for instance in amount of about 10-50% by weight.

When the oral composition is a toothpaste, the dental vehicle contains as a solid portion, a gelling agent. The gelling agent includes alkali metal carboxymethyl cellulose, carrageenans such as viscarin and i-carrageenan, gelatin, starch, glucose, sucrose, polyvinyl pyrollidone, polyvinyl alcohol, gums such as gum tragacanth and gum karaya, hydroxypropyl cellulose, methyl cellulose, carboxyethyl cellulose, sodium alginate, synthetic inorganic complex silicate clays and magnesium aluminum silicate gel, as well as mixtures thereof. The solid portion or gelling agent of the vehicle is typically present in amount of about 0.25-10% by weight. Alkali metal carboxymethyl cellulose includes the lithium, sodium and potassium salts. Sodium carboxymethyl cellulose is preferred.

Any suitable substantially water-insoluble polishing agent may be added to the dental vehicle of a toothpaste. There is a relatively large number of such materials known in the art. Representative materials include, for example, dicalcium phosphate, tricalcium phosphate, insoluble sodium metaphosphate, silica, sodium aluminosilicate (silica containing combined alumina), aluminum hydroxide, magnesium carbonate, calcium carbonate, calcium pyrophosphate, calcium sulfate, bentonite, etc., including suitable mixtures thereof. It is preferred to use the water-insoluble phosphate, sodium metaphosphate and/or a calcium phosphate, such as dicalcium phosphate dihydrate. In general, these polishing agents will comprise a major proportion by weight of the solid ingredients. The polishing agent content is variable, but will generally be up to about 75% by weight of the total composition, generally about 20-75%; although even lower amounts of polishing agent can be employed.

Any suitable or compatible surface-active or detersive material may be incorporated in the dental vehicle. Such compatible materials are desirable to provide additional detersive, foaming and antibacterial properties depending upon the specific type of surface-active material and are selected similarly. These detergents are water-soluble organic compounds usually, and may be anionic, nonionic, or cationic in structure. It is preferred to use the water-soluble non-soap or synthetic organic detergents usually. Suitable detersive materials are known and include, for example, the water-soluble salts of higher fatty acid monoglyceride monosulfate detergent (e.g., sodium coconut fatty acid monoglyceride monosulfate), higher alkyl sulfates (e.g., sodium lauryl sulfate), alkyl aryl sulfonate (e.g., sodium dodecyl benzene sulfonate), methylcocoyl laureate, higher fatty acid esters of 1,2-dihydroxypropanesulfonate) and the like.

The following examples serve to provide further appreciation of the invention but are not meant in any way to restrict the effective scope of the invention. All percentages throughout the specification are by weight percent of the final delivery system unless otherwise indicated.

EXAMPLE 1

In this example, a coated particle was prepared comprising a core material of zinc gluconate. Zinc gluconate was prepared by standard methods into particular form and was then milled through a 30 mesh screen. The resulting particles were then coated by fluidized bed coating procedure in a Verse Glatt fluidized bed coater with the top spray method as disclosed hereinabove. Accordingly, 56.25 grams of 250 bloom gelatin was prepared as a 7% by weight aqueous solution, and it was then applied to 500 grams of the zinc gluconate milled powder. The process was continued until larger particles were formed, whereupon it was found that the gelatin solution was more capable of coating the resulting formed particles.

EXAMPLE 2

A similar particulate product was prepared using the same procedure set forth in Example 1, above. In this instance, the zinc compound comprised zinc sulfate powder which had likewise been milled through a 30 mesh screen. The coating was again 250 bloom gelatin, in this instance prepared to a 15% solution, and in particular, 180 grams of gelatin was prepared and applied to 1200 grams of the core material. A similar result was achieved.

EXAMPLE 3

In this example, a core material of the type prepared in Example 2 above was further coated to form the plural coated product of the present invention. Accordingly, the zinc sulfate encapsulated by gelatin as set forth in Example 2 above served as the core material to which a coating of 50% by weight of a mixture of 95% by weight of hydrogenated soybean oil and 5% by weight of glycerol monostearate was applied. In this instance, a fluidized bed coating procedure with a top spray method was utilized, and 600 grams of the zinc sulfate core was coated with 300 grams of the coating solution.

EXAMPLE 4

In this preparation, a core material comprising 50% of a zinc sulfate powder milled to 30 mesh and 50% of maltodextrin was first prepared, after which a 10% solution of 250 bloom gelatin was applied by fluidized bed procedures as set forth in Example 1. Thus, 1000 grams of the core material was coated with 100 grams of the gelatin as dispersed in the solution to form the singly coated particles similar to those prepared in Examples 1 and 2, above.

EXAMPLE 5

In this example, a plurally coated particle was prepared by first preparing a core material comprising 22.3% zinc gluconate powder as milled to 30 mesh, 8,9% maltodextrin and 58.1% 6X-sugar. 10.7% by weight of 250 bloom gelatin was applied to this material to form the core material with the first hydrophilic coating. This material was then coated with a coating material comprising 95% by weight of hydrogenated soybean oil and 5% by weight of glycerol monostearate in an amount by weight of 50% of the initially coated core material. Thus, 600 grams of the core material comprising the zinc gluconate-maltodextrin-sugar particle coated with gelatin was coated with a solution equivalent to 300 grams of hydrogenated soybean oil/glycerol monostearate to form the final plural coated particle.

EXAMPLE 6

In this example, a core material comprising 35% zinc gluconate powder milled through a 30 mesh screen and 65% maltodextrin was coated with 10% by weight of 250 bloom gelatin by the fluidized bed coating procedure set forth in Example 1. Thus, 1000 grams of the core material was coated with a solution containing 100 grams of gelatin to form the initially coated zinc compound.

EXAMPLE 7

In this example, a composite zinc compound core material was prepared comprising 22.7% of zinc sulfate powder milled through a 30 mesh screen, 9.1% maltodextrin and 59.1% fructose. This composite particle was then coated with 9.1% of 250 bloom gelatin to form the initial coated particle. These particles were then subjected to a second fluidized bed coating procedure with 50% by weight of the coated particles of a coating material itself comprising 95% by weight of hydrogenated soybean oil and 5% by weight of glycerol monostearate. Accordingly, 600 grams of the core material comprising the gelatin coated zinc compound as described was coated with 300 grams of the hydrogenated soybean oil/glycerol monostearate mixture to form the final dually coated particles.

EXAMPLE 8

In this example, lozenges were prepared by standard procedures for hard candy formulation. The lozenges weighed 2.2 grams each and contained corn syrup, sugar, water and 6500 ppm of zinc. The control samples contained zinc gluconate in its free form, while the inventive lozenges contained zinc gluconate that was dually encapsulated as described earlier herein. The resulting lozenges were then subjected to blind testing by a panel to compare the attributes of astringency/dryness, roughness and bitterness. Roughness was evaluated as a function of the feel of the lozenge on the surface of the tongue, and higher numerical ratings indicated a correspondingly greater perception of the evaluated attribute. The panel tested each sample and rated it in each of the categories at intervals of 30 seconds, 1 minute, 2 minutes, 3 minutes and 4 minutes. The results of the comparative evaluations of each of the attributes are separately depicted, with astringency/dryness presented in FIG. 1, roughness in FIG. 2, and bitterness in FIG. 3.

Figure 1:
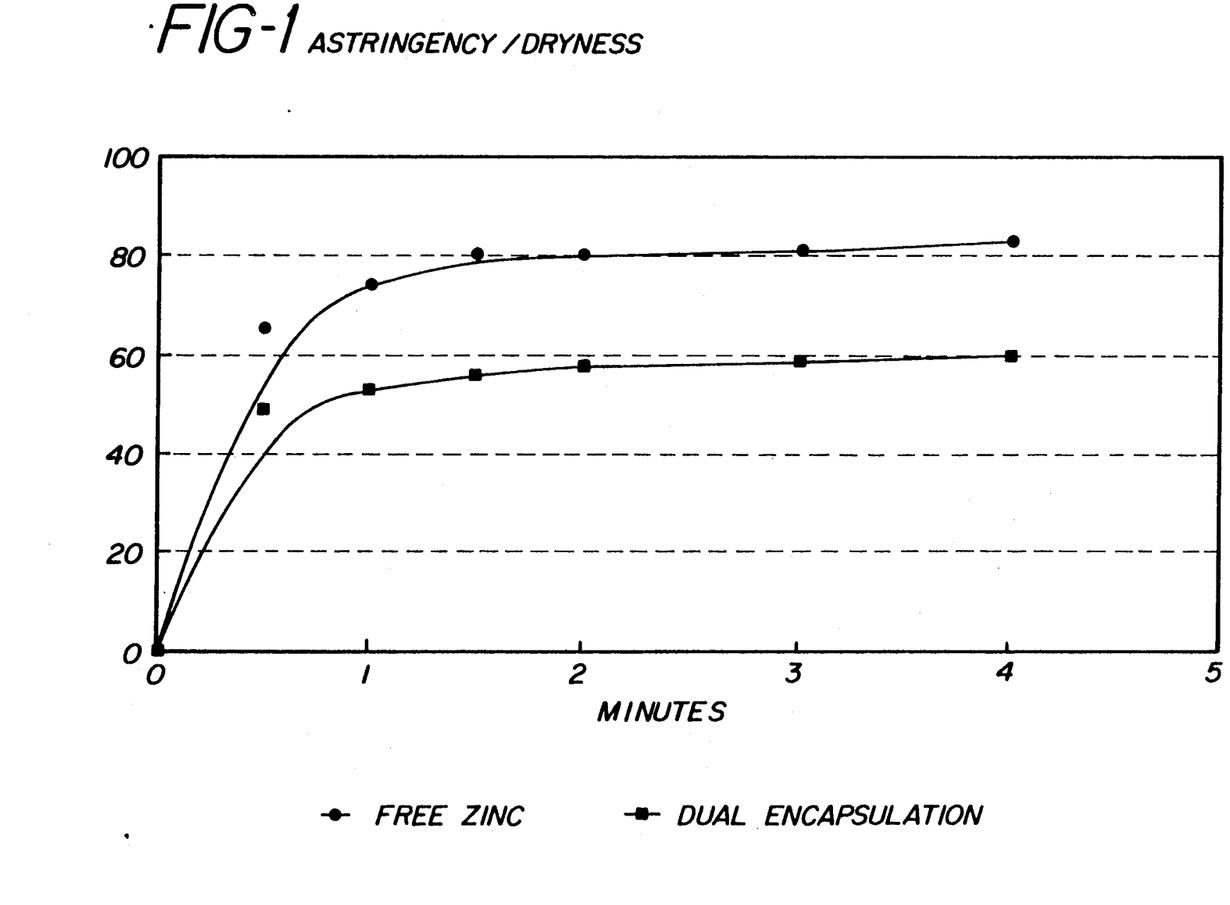
FIG. 1 is a graph presenting the results of comparative sensory evaluation of the astringency/dryness of lozenges containing the present invention over control lozenges containing the same zinc compound in free form.
Figure 2:
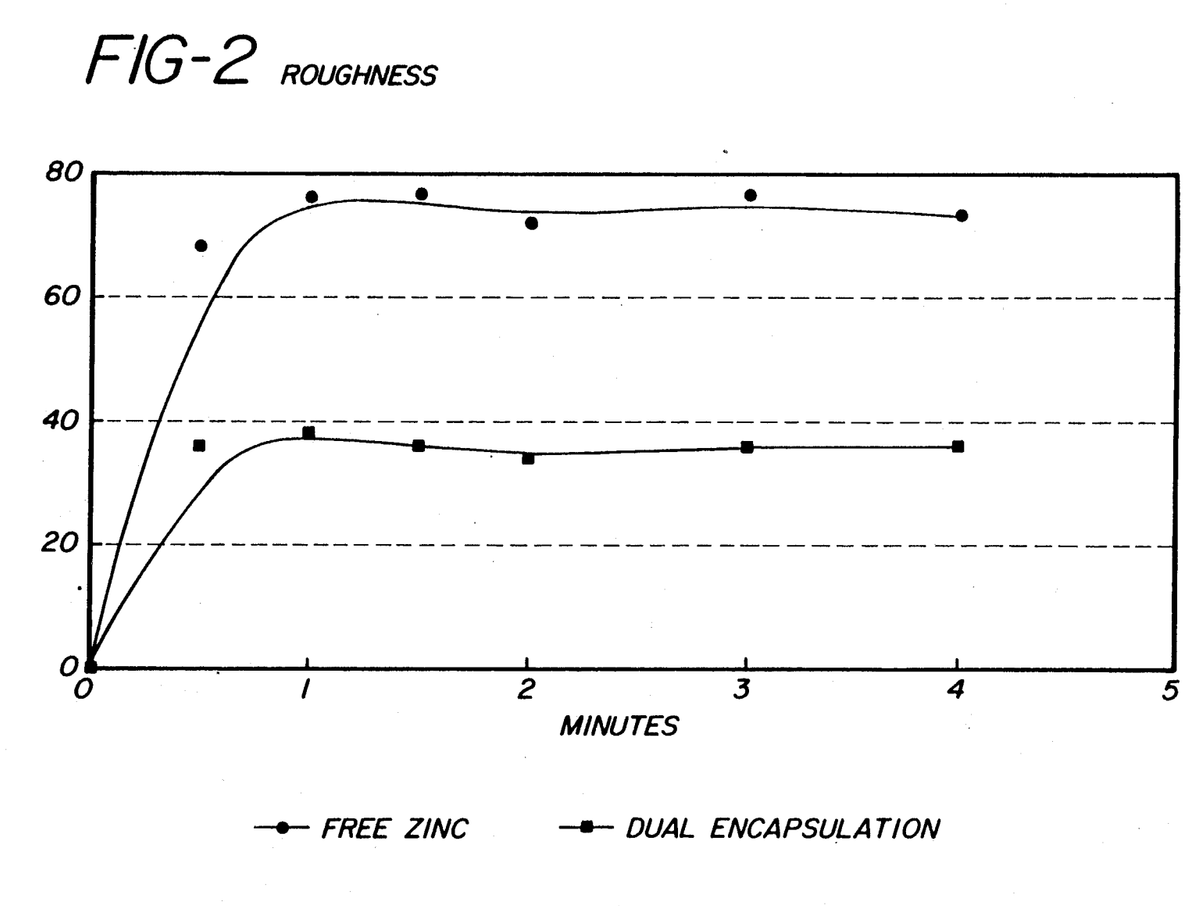
FIG. 2 is a graph presenting the results of comparative sensory evaluation of the roughness of the lozenges compared in FIG. 1.
Figure 3:
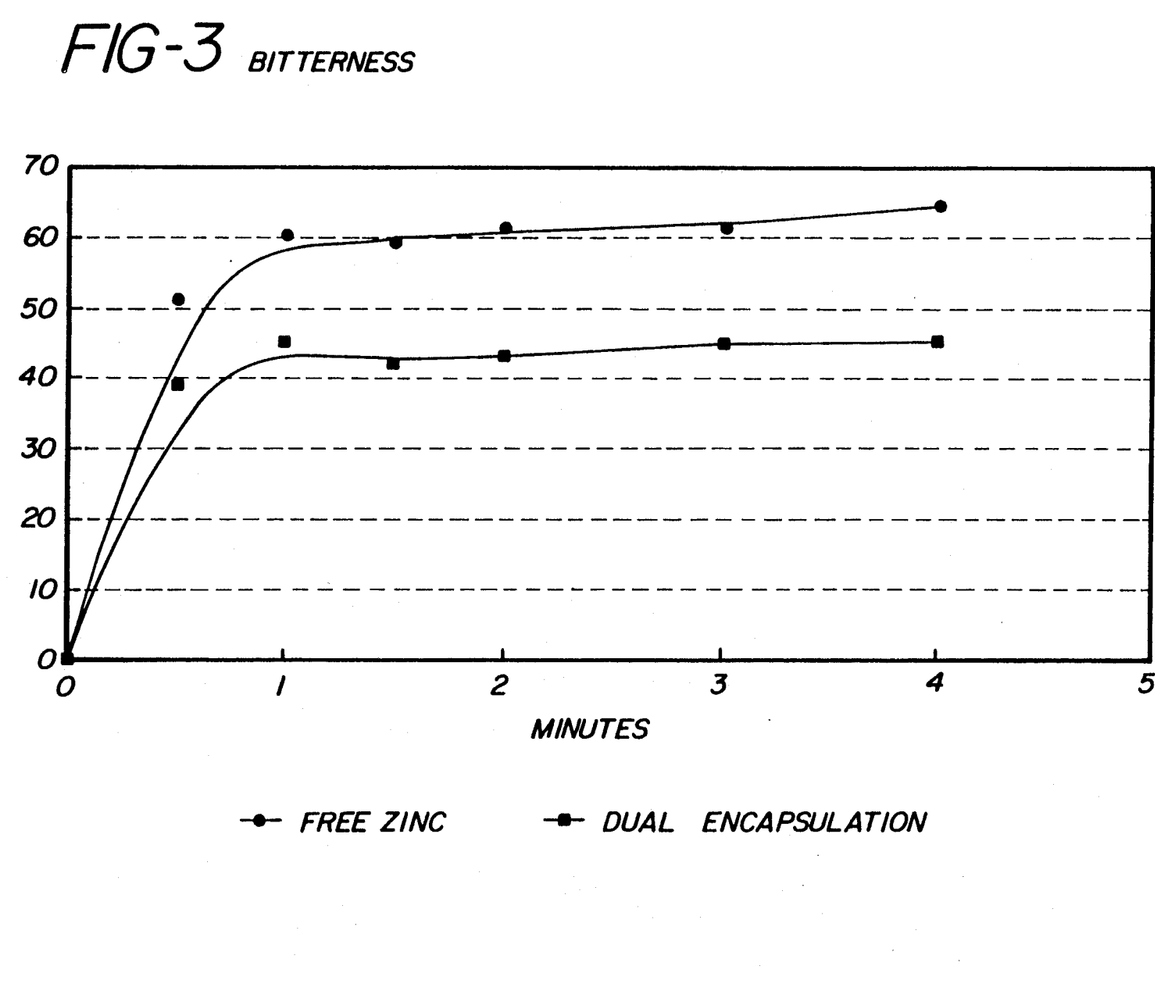
FIG. 3 is a graph presenting the results of comparative sensory evaluation of the bitterness of the lozenges compared in FIG. 1.

From the Figures, it is apparent that the materials possessing the double encapsulation and thereby representative of the delivery system of the present invention exhibited lower levels of roughness, bitterness and dryness. The sensations of both bitterness and dryness were increased when the undesirable taste of the zinc compound was released and experienced. Thus, the present encapsulated products offer superior taste masking qualities.

The quality of dryness is, to some extent, a function of the astringency of the zinc compound. The improved encapsulation achieved by the present zinc delivery system promoted reduced dryness and bitterness in combination with improved smoothness when the inventive lozenges were dissolved in the mouth.

This invention may be embodied in other forms or carried out in other ways without departing from the spirit or essential characteristics thereof. The present disclosure is therefore to be considered as in all respects illustrative and not restrictive, the scope of the invention being indicated by the appended claims, and all changes which come within the meaning and range of equivalency are intended to be embraced therein.

What is claimed is:

1. A delivery system for a zinc salt providing reduced bitterness with improved mouthfeed and high temperature stability, comprising:
   (a) a core material comprising a zinc salt selected from the group consisting of inorganic salts of zinc, organic salts of zinc and mixtures thereof;
   (b) a first hydrophilic coating comprising a hydrocolloid material in an amount of from about 10% to about 50% by weight of said core material; and (c) a second hydrophobic coating selected from the group consisting of fats, fatty acids, waxes and mixtures thereof, present in an amount ranging from about 20% to about 100% by weight of the combination of said core material and said first hydrophilic coating.

2. A delivery system of claim 1 wherein said inorganic salts of zinc are selected from the group consisting of zinc bromide, zinc chloride, zinc iodine, zinc fluoride, zinc ammonium sulfate, zinc chromate, zinc fluorosilicate, zinc dithionate, zinc sulfate, zinc nitrate, zinc phosphate, zinc fluorozirconate, zinc oxide, and mixtures thereof.

3. The delivery system of claim 1 wherein said organic salts of zinc are selected from the group consisting of zinc citrate, zinc acetate, zinc gluconate, zinc asparate, zinc ascorbate, zinc oroate, zinc divalent amino acid zinc salts, zinc succinate, zinc tartrate, zinc glycerophosphate, zinc salicylate, zinc formate, and mixtures thereof.

4. The delivery system of any one of claims 1-3 further including an excipient.

5. The delivery system of claim 4 wherein said excipient is selected from the group consisting of carbohydrate materials, polyhydric alcohols, and mixtures thereof.

6. The delivery system of claim 4 wherein said excipient is selected from the group consisting of monosaccharides, disaccharides, polysaccharides, partially hydrolyzed starch, corn syrup solids, sugar alcohols, and mixtures thereof.

7. The delivery system of claim 4 wherein said excipient is present in an amount of from about 1% to about 80% by weight of said core material.

8. The delivery system of claim 1 wherein said hydrocolloid is selected from the group consisting of gums, pectins, alginates, and mixtures thereof.

9. The delivery system of claim 8 wherein said hydrocolloid is selected from the group consisting of gum arabic, tragacanth, karaya, ghatti, agar, alginates, carrageenans, furcellaran, psyllium, and mixtures thereof.

10. The delivery system of claim 8 wherein said hydrocolloid is selected from the group consisting of polyvinyl pyrrolidone, gelatin, dextran, xanthan, curdan, cellulose, methylcellulose, ethylcellulose, hydroxyethyl cellulose, hydroxypropyl cellulose, hydroxypropyl methylcellulose, carboxymethyl cellulose, low methoxy pectin, propylene glycol alginate, and mixtures thereof.

11. The delivery system of claim 1 wherein said first coating is present in an amount of from about 10% to about 25% by weight of the core material.

12. The delivery system of claim 1 wherein said second coating is present in an amount of from about 20% to about 50% by weight of the combination of the core material and the first coating.

13. The delivery system of claim 1 wherein said first coating is present in an amount of 25% by weight of the core material and said second coating is present in an amount of 50% by weight of the combination of the core material and the first coating.

14. The delivery system of claim 1 wherein the fat is a fatty acid is selected from the group consisting of hydrogenated and partially hydrogenated oils.

15. The delivery system of claim 14 wherein the hydrogenated or partially hydrogenated oils are selected from the group consisting of palm oil, palm kernel oil, soybean oil, rapeseed oil, rice bran oil, cottonseed oil, sunflower oil, safflower oil, and mixtures thereof.

16. The delivery system of claim 1 wherein the fat is selected from the group consisting of monoglycerides, diglycerides, triglycerides, polyglycerol esters, sorbitol esters, and mixtures thereof.

17. The delivery system of claim 1 wherein the wax is selected from the group consisting of natural waxes, synthetic waxes and mixtures thereof.

18. The delivery system of claim 17 wherein the wax is selected from the group consisting of paraffin wax beeswax, carnauba wax, candelilla wax, lanolin wax, bayberry wax, sugar cane wax, petrolatum, polyethylene glycol, spermaceti wax, rice bran wax, and mixtures thereof.

19. The delivery system of claim 1 incorporated into a chewing gum composition.

* * * * *